US006403813B1

(12) United States Patent
Petersen et al.

(10) Patent No.: US 6,403,813 B1
(45) Date of Patent: Jun. 11, 2002

(54) METHOD FOR THE PREPARATION OF 5-CARBOXYPHTHALIDE

(75) Inventors: Hans Petersen, Vanløse; Poul Dahlberg Nielsen, Vig, both of (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/692,653

(22) Filed: Oct. 19, 2000

(30) Foreign Application Priority Data

Nov. 1, 1999 (DK) .............................. 01569/99

(51) Int. Cl.[7] ..................... C07D 307/00; C07D 307/77
(52) U.S. Cl. ........................................ 549/305
(58) Field of Search ......................... 549/305

(56) References Cited

U.S. PATENT DOCUMENTS

| | | | |
|---|---|---|---|
| 3,467,675 A | 9/1969 | Petersen et al. | 260/346.2 |
| 4,136,193 A | 1/1979 | Bøgesø et al. | 424/285 |
| 4,650,884 A | 3/1987 | Bogeso | 549/467 |
| 4,943,590 A | 7/1990 | Boegesoe et al. | 415/469 |
| 6,020,501 A * | 2/2000 | Massonne et al. | 549/307 |
| 6,028,204 A * | 2/2000 | Massonne et al. | 549/307 |
| 6,229,026 B1 | 5/2001 | Petersen | 549/467 |
| 6,258,842 B1 | 7/2001 | Petersen et al. | 514/469 |
| 6,291,689 B1 | 9/2001 | Petersen et al. | 549/467 |

FOREIGN PATENT DOCUMENTS

| | | | |
|---|---|---|---|
| EP | 171 943 | 1/1986 | ......... C07C/121/80 |
| EP | 1 095 926 | 5/2001 | ......... C07C/33/46 |
| WO | 99/30548 | 6/1999 | |
| WO | 00/11926 | 3/2000 | |
| WO | 00/12044 | 3/2000 | |
| WO | 00/13648 | 3/2000 | |
| WO | 00/23431 | 4/2000 | ......... C07D/307/87 |
| WO | 00/39112 | 7/2000 | ......... C07D/307/87 |
| WO | 00/44738 | 8/2000 | ......... C07D/307/88 |

OTHER PUBLICATIONS

Forney, L.S., J. Org. Chem. vol. 35, p. 1695–1696, 1970.*
U.S. application No. 09/794,762, filed Feb. 26, 2001.
U.S. application No. 09/794,755, filed Feb. 26, 2001.
U.S. application No. 09/830,109, filed Jun. 1, 2001.
U.S. application No. 09/888,067, filed Dec. 22, 1999.
U.S. application No. 09/891,874, filed Oct. 25, 1999.
U.S. application No. 09/917,180, filed Jan. 26, 2000.
U.S. application No. 09/977,920, filed Oct. 15, 2001.
Bigler, Allan J. et al., "Quantitative structure–activity relationship in a series of selective 5–HT uptake inhibitors," *Eur. J. Med. Chem.—Chimica Therapeutica* 12, 3: 289–295 (May–Jun. 1977).
Buehler, Calvin A., et al., Survey of Organic Syntheses, 951 (John Wiley & Sons, 1970).
Barton, Sir Derek, F.R.S. et al., "vol. 2 Nitrogen Compounds, Carboxylic Acids, Phosphorus Compounds", in Comprehensive Organic Chemistry—The Synthesis and Reactions of Organic Compounds, vol. II, pp. 1024–1025 (1979).
Levy, Leopold F., "4–Aminophthalide and Some Derivatives", *J. Chem. Soc.* pp. 867–870, (1931).
J. Tirouflet, "Phtalide Substitutes en 5," *Bulb. Soc. Sci. de Bretagne*, 26: 35–43 (1951).

* cited by examiner

*Primary Examiner*—Floyd D. Higel
*Assistant Examiner*—Golam M.M. Shameem
(74) *Attorney, Agent, or Firm*—Darby & Darby

(57) ABSTRACT

5-carboxyphthalide is obtained with very high purity and in high yields by a convenient process comprising reaction of terephthalic acid

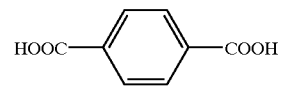

with paraformaldehyde $HO(CH_2)_nH$ in oleum.

6 Claims, No Drawings

METHOD FOR THE PREPARATION OF 5-CARBOXYPHTHALIDE

The present invention relates to a novel process for the preparation of 5-carboxyphthalide, a starting material for the manufacture of the well-known antidepressant drug citalopram, 1-[3-(dimethylamino)propyl]-1-(4fluorophenyl)-1,3-dihydro-5-isobenzofurancarbonitrile.

BACKGROUND OF THE INVENTION

Citalopram is a selective serotonin reuptake inhibitor which has successfully been marketed as an antidepressant drug for some years, It has the following structure:

Formula I

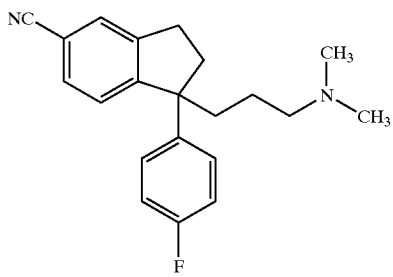

and it may be prepared by the process described in U.S. Pat. No. 4,650,894 according to which 5-cyanophthalide is subjected to two successive Grignard reactions, i.e. with 4-fluoro-phenyl magnesium halogenide and N,N-dimethylaminopropyl magnesium halogenide, respectively, and the resulting dicarbinol compound is subjected to a ring closure reaction by dehydration. The 5-cyanophthalide may in its turn be obtained by reaction of 5-carboxyphthalide with a dehydrating agent and a sulfonamide of the formula $H_2N-SO_2-R$ wherein R is $NH_2$, alkyloxy, optionally substituted phenyloxy, or substituted phenyl in order to obtain 5-cyanophthalide, cf. our co-pending Danish patent application No. PA199801718.

5-Carboxyphthalide has been described as a useful intermediate in the polymer and paint industry. However, no reliable commercial source is available at present. A known process comprises catalytic hydrogenation of trimellithic acid (DE-A1 2630927). This process provides a mixture of the 5- and 6-carboxyphthalides and, accordingly, it requires elaborate and costly purification. According to J. Org. Chem. 1970, 35, p. 1695–1696, 5-carboxyphthalide is synthesised by reaction of terephthalic acid with trioxane in liquid $SO_3$. During this process, trioxane sublimates and precipitates thereby obstructing the equipment.

Though a number of other methods failed, it has now been found that 5-carboxyphthalide may be prepared from terephthalic acid in high yields by a convenient, cost-effective procedure.

DESCRIPTION OF THE INVENTION

Accordingly, the present invention provides a process for the manufacture of 5-carboxyphthalide

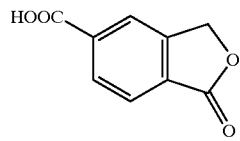

comprising reaction of terephthalic acid

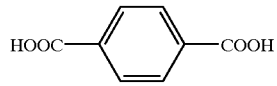

with paraformaldehyde, $HO(CH_2)_nH$, in oleum.

By the process of the invention, 5-carboxyphthalide is obtained with very high purity and in high yields (>about 75%). Furthermore, as compared with the prior art process (J. Org. Chem. 1970, 35, p. 1695–1696), the process of the invention takes place without precipitation of sublimated trioxane which obstructs the equipment e.g. by precipitating in condensers.

The oleum used is commercially available oleum. So the following are available from Aldrich/Fluka:
12–17% $SO_3$ (Fuming sulfuric acid)=15% oleum
18–24% $SO_3$ (Fuming sulfuric acid)=20% oleum
27–33% $SO_3$ (Fuming sulfuric acid)=30% oleum
From other sources 20% oleum contains 20–25% $SO_3$ In the method of the invention, the terephthalic acid is condensed with paraformaldehyde liberating water, which reacts with the $SO_2$. When the reaction is complete, 5-carboxyphthalide may be isolated as follows: The reaction mixture is hydrolysed with water. The condensed product, 5-carboxyphthalide inclusive possible diphthalide impurities may then be filtered off, and the 5-carboxyphthalide may be dissolved in aqueous medium by adjusting pH to about 6.7 to 7.3, leaving possible diphthalide impurities in the solid phase. The diphthalide present may be filtered off whereupon 5-carboxyphthalide may be precipitated by acidification, filtered off, washed with water and dried.

Preferably 1.0–1.33 equivalents $CH_2O$ and 1.0–2.5, preferably 1.0–2.0 are used. More preferably 1.25–1.5 equivalents $SO_3$ per equivalent terephthalic acid are used. Most preferably, about 1.37 equivalents (corresponding to about 3.3 kg 20–25% oleum/kg terephthalic acid) are used per equivalent terephthalic acid.

The reaction of terephthalic acid with paraformaldehyde is carried out at elevated temperature, conveniently at about 50–148° C., preferably 115–125° C. or 138–148° C. The reaction time is not critical and may easily be determined by a person skilled in the art, a reaction time of 17–21 hours is preferably used for a 210 kg batch at 115–125° C. The time is decreased with increasing temperature.

The adjustment of pH to 6.3 to 7.3 in order to dissolve the 5-carboxyphthalide formed may be effected by NaOH, e.g. about 10% aqueous NaOH.

Acidification in order to precipitate the 5-carboxyphthalide may be carried out by adding sulphuric acid until pH=2.

The terephthalic acid used as a starting material is commercially available.

EXAMPLES

The invention is further illustrated by the following example.

Example 1

5-Carboxyphthalid

Terephthalic acid (10 kg) is charged into a reactor. Oleum (20% (18–24% $SO_3$); 6 kg/kg terephthalic acid ) is added and then paraformaldehyde (1.33 equivalents, 0.24 kg/kg terephthalic acid) is added. The mixture is agitated at 125° C. for 17 hours. Water (13 kg/kg terephthalic acid and filter aid is added, the temperature is adjusted to about 70° C. The precipitate is filtered of, washed with water and suspended in water. The pH of the suspension is adjusted to about 7 with NaOH, activated carbon, 0.07 kg/kg terephthalic acid is added, and then the mixture is filtered, the precipitate is rinsed with water. The temperature of the filtrate is adjusted to about 65° C. and the pH is adjusted to about 2 with 50% sulfuric acid. The 5-carboxyphthalide precipitated is separated by filtration washed and dried. Yield 83%.

Example 2

5-Carboxyphthalid

Oleum (20–25% $SO_3$ 43 kg) is charged into a reactor. Terephthalic acid (13 Kg) and then paraformaldehyde (3.8 Kg) is added. The mixture is agitated at 138–148° C. for 4½ hours. Water (87 L) is added and the temperature is adjusted to about 100° C. The precipitate is filtered of, washed with water and suspended in water. The pH of the suspension is adjusted to about 7 with NaOH (about 10%), activated carbon, 0.5 Kg is added, and then the mixture is filtered, the precipitate is rinsed with water. The temperature of the filtrate is adjusted to about 85° C. and the pH is adjusted to about 2 with 96% sulfuric acid. The 5-carboxyphthalide precipitated is separated by filtration washed and dried. Yield 82%.

What is claimed is:

1. A method for the preparation of 5-carboxyphthalide

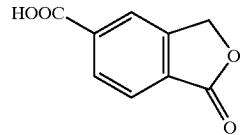

comprising reaction of terephthalic acid

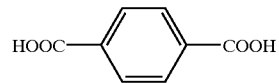

with paraformaldehyde $HO(CH_2)_nH$ in oleum.

2. The method of claim 1 wherein 1.0–1.33 equivalents $CH_2O$ and 1.0–2.5 equivalents $SO_3$ per equivalent terephthalic acid are used.

3. The method of claim 2 wherein 1.0–2.0 equivalents $SO_3$ per equivalent terephthalic acid are used.

4. The method of claim 3 wherein about 1.37 equivalents $SO_3$ per equivalent terephthalic acid are used.

5. The method of claim 3 wherein about 3.3 kg 20–25% oleum is used per kg terephthalic acid.

6. The method of claim 3 wherein 1.25–1.5 equivalents $SO_3$ per equivalent terephthalic acid are used.

* * * * *

UNITED STATES PATENT AND TRADEMARK OFFICE
CERTIFICATE OF CORRECTION

PATENT NO. : 6,403,813 B1
DATED : June 11, 2002
INVENTOR(S) : Hans Petersen et al.

It is certified that error appears in the above-identified patent and that said Letters Patent is hereby corrected as shown below:

Title page,
Item [57], ABSTRACT,
Line 5, delete "$HO(CH_2)_nH$" and replace with -- $HO(CH_2O)_nH$ --.

Column 1,
Line 9, delete "(4fluorophenyl)" and replace with -- (4-fluorophenyl) --.
Lines 20-25, delete

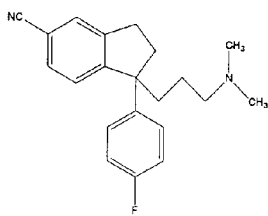

and replace with

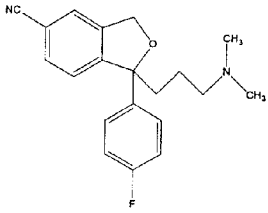

Line 32, delete "4,650,984" and replace with -- 4,650,884 --.

Column 2,
Line 16, delete "$HO(CH_2)_nH$" and replace with -- $HO(CH_2O)_nH$ --.

Column 3,
Lines 2 and 19, delete "5-Carboxyphthalid" and replace with -- 5-Carboxyphthalide --.
Lines 9 and 24, delete "of" and replace with -- off --.

UNITED STATES PATENT AND TRADEMARK OFFICE
CERTIFICATE OF CORRECTION

PATENT NO. : 6,403,813 B1
DATED : June 11, 2002
INVENTOR(S) : Hans Petersen et al.

It is certified that error appears in the above-identified patent and that said Letters Patent is hereby corrected as shown below:

Column 4,
Line 18, delete "$HO(CH_2)_nH$" and replace with -- $HO(CH_2O)_nH$ --.

Signed and Sealed this

Twenty-third Day of September, 2003

JAMES E. ROGAN
*Director of the United States Patent and Trademark Office*